United States Patent
Mansfield (10) Patent No.: US 10,960,231 B2
(45) Date of Patent: Mar. 30, 2021

(54) RADIATION THERAPY SYSTEMS AND METHODS

(71) Applicant: Varian Medical Systems, Inc., Palo Alto, CA (US)

(72) Inventor: Stanley Mansfield, Sunnyvale, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 16/401,387

(22) Filed: May 2, 2019

(65) Prior Publication Data
US 2019/0255361 A1 Aug. 22, 2019

Related U.S. Application Data

(63) Continuation of application No. 15/850,472, filed on Dec. 21, 2017, now Pat. No. 10,307,618, which is a
(Continued)

(51) Int. Cl.
*A61N 5/10* (2006.01)

(52) U.S. Cl.
CPC ......... *A61N 5/1077* (2013.01); *A61N 5/1043* (2013.01); *A61N 5/1049* (2013.01);
(Continued)

(58) Field of Classification Search
CPC .... A61N 2005/1087; A61N 2005/1095; A61N 5/1067; A61N 5/1043; A61N 5/1049; A61N 5/1077; A61N 5/1042; A61N 2005/1074; A61N 5/10; A61N 2005/1061; A61N 5/1044; A61N 5/1064; A61N 5/1075;
(Continued)

(56) References Cited

U.S. PATENT DOCUMENTS

| 6,222,544 B1 | 4/2001 | Tarr et al. |
| 6,260,005 B1 | 7/2001 | Yang et al. |

(Continued)

FOREIGN PATENT DOCUMENTS

| CN | 1161240 | 10/1997 |
| CN | 1997256 | 7/2007 |

(Continued)

OTHER PUBLICATIONS

Ultrahigh dose-rate FLASH irradiation increases the differential response between normal and tumor tissue in mice Favaudon, et al. Research Article, www.sciencetranslationalmedicine.org Jul. 16, 2014, vol. 6 Issue 245 pp. 1-9.
(Continued)

*Primary Examiner* — David A Vanore (57) ABSTRACT

A radiation therapy system includes an accelerator and beam transport system that generates a beam of particles. The accelerator and beam transport system guides the beam on a path and into a nozzle that is operable for aiming the beam toward an object. The nozzle includes a scanning magnet operable for steering the beam toward different locations within the object, and also includes a beam energy adjuster configured to adjust the beam by, for example, placing different thicknesses of material in the path of the beam to affect the energies of the particles in the beam.

19 Claims, 7 Drawing Sheets

Related U.S. Application Data continuation of application No. 15/089,330, filed on Apr. 1, 2016, now Pat. No. 9,855,445.

(52) U.S. Cl.
CPC .... *A61N 5/1067* (2013.01); *A61N 2005/1087* (2013.01); *A61N 2005/1095* (2013.01)

(58) Field of Classification Search
CPC .... G21K 5/04; G21K 1/10; G21K 1/043; G21K 1/093; H05H 7/10; H05H 7/00
USPC ......... 250/492.3, 396 R, 398, 370.09, 492.1, 250/505.1; 378/145, 65, 9
See application file for complete search history.

(56) References Cited

U.S. PATENT DOCUMENTS

| | | | | |
|---|---|---|---|---|
| 6,379,380 | B1 | 4/2002 | Satz | |
| 6,411,675 | B1 | 6/2002 | Llacer | |
| 6,504,899 | B2 | 1/2003 | Pugachev et al. | |
| 6,617,598 | B1* | 9/2003 | Matsuda | G21K 5/04 250/398 |
| 6,777,700 | B2* | 8/2004 | Yanagisawa | A61N 5/1042 250/492.3 |
| 6,847,700 | B1 | 1/2005 | Mitra et al. | |
| 6,993,112 | B2 | 1/2006 | Hesse | |
| 7,026,636 | B2* | 4/2006 | Yanagisawa | A61N 5/1042 250/492.3 |
| 7,049,613 | B2* | 5/2006 | Yanagisawa | G21K 1/10 250/492.3 |
| 7,071,479 | B2* | 7/2006 | Yanagisawa | A61N 5/1042 250/492.3 |
| 7,102,144 | B2* | 9/2006 | Matsuda | A61N 5/10 250/492.1 |
| 7,227,161 | B2 | 6/2007 | Matsuda et al. | |
| 7,268,358 | B2 | 9/2007 | Ma et al. | |
| 7,285,203 | B2 | 10/2007 | Russell et al. | |
| 7,297,967 | B2* | 11/2007 | Yanagisawa | A61N 5/1042 250/492.3 |
| 7,385,203 | B2 | 6/2008 | Nakayama et al. | |
| 7,397,054 | B2 | 7/2008 | Natori et al. | |
| 7,449,701 | B2* | 11/2008 | Fujimaki | A61N 5/10 250/492.3 |
| 7,453,983 | B2 | 11/2008 | Schildkraut et al. | |
| 7,456,415 | B2 | 11/2008 | Yanagisawa et al. | |
| 7,515,681 | B2 | 4/2009 | Ebstein | |
| 7,550,752 | B2 | 6/2009 | Keppel et al. | |
| 7,560,715 | B2* | 7/2009 | Pedroni | A61N 5/10 250/398 |
| 7,589,334 | B2 | 9/2009 | Hiramoto et al. | |
| 7,590,219 | B2 | 9/2009 | Maurer, Jr. et al. | |
| 7,616,735 | B2 | 11/2009 | Maciunas et al. | |
| 7,623,623 | B2 | 11/2009 | Raanes et al. | |
| 7,659,521 | B2* | 2/2010 | Pedroni | A61N 5/1049 250/370.09 |
| 7,755,305 | B2* | 7/2010 | Umezawa | A61N 5/10 250/396 R |
| 7,778,691 | B2 | 8/2010 | Zhang et al. | |
| 7,807,982 | B2 | 10/2010 | Nishiuchi et al. | |
| 7,825,388 | B2* | 11/2010 | Nihongi | A61N 5/1048 250/492.3 |
| 7,831,289 | B2 | 11/2010 | Riker et al. | |
| 7,835,492 | B1 | 11/2010 | Sahadevan | |
| 7,875,868 | B2 | 1/2011 | Moriyama et al. | |
| 8,030,627 | B2 | 10/2011 | Gentry et al. | |
| 8,039,819 | B2 | 10/2011 | Faure et al. | |
| 8,106,371 | B2* | 1/2012 | Fujii | A61N 5/1044 250/492.3 |
| 8,129,699 | B2 | 3/2012 | Balakin | |
| 8,198,607 | B2 | 6/2012 | Balakin | |
| 8,253,113 | B2 | 8/2012 | Nishiuchi et al. | |
| 8,263,954 | B2 | 9/2012 | Iwata | |
| 8,395,131 | B2 | 3/2013 | Wu et al. | |
| 8,401,148 | B2 | 3/2013 | Lu et al. | |
| 8,406,844 | B2 | 3/2013 | Ruchala et al. | |
| 8,559,596 | B2 | 10/2013 | Thomson et al. | |
| 8,600,003 | B2 | 12/2013 | Zhou et al. | |
| 8,613,694 | B2 | 12/2013 | Walsh | |
| 8,618,521 | B2 | 12/2013 | Loo et al. | |
| 8,636,636 | B2 | 1/2014 | Shukla et al. | |
| 8,644,571 | B1 | 2/2014 | Schulte et al. | |
| 8,658,991 | B2 | 2/2014 | Pu et al. | |
| 8,716,663 | B2 | 5/2014 | Brusasco et al. | |
| 8,754,386 | B2 | 6/2014 | Iwata | |
| 8,829,476 | B2 | 9/2014 | Keppel et al. | |
| 8,847,179 | B2 | 9/2014 | Fujitaka et al. | |
| 8,948,341 | B2 | 2/2015 | Beckman | |
| 8,986,186 | B2 | 3/2015 | Zhang et al. | |
| 8,995,608 | B2 | 3/2015 | Zhou et al. | |
| 9,018,603 | B2 | 4/2015 | Loo et al. | |
| 9,033,859 | B2 | 5/2015 | Fieres et al. | |
| 9,108,050 | B2* | 8/2015 | Bula | A61N 5/1044 |
| 9,149,656 | B2 | 10/2015 | Tanabe | |
| 9,155,908 | B2 | 10/2015 | Meltsner et al. | |
| 9,233,260 | B2 | 1/2016 | Slatkin et al. | |
| 9,283,406 | B2 | 3/2016 | Prieels | |
| 9,308,391 | B2 | 4/2016 | Liu et al. | |
| 9,333,374 | B2 | 5/2016 | Iwata | |
| 9,517,358 | B2 | 12/2016 | Velthuis et al. | |
| 9,545,444 | B2 | 1/2017 | Strober et al. | |
| 9,636,381 | B2 | 5/2017 | Basile | |
| 9,636,525 | B1 | 5/2017 | Sahadevan | |
| 9,649,298 | B2 | 5/2017 | Djonov et al. | |
| 9,656,098 | B2 | 5/2017 | Goer | |
| 9,694,204 | B2 | 7/2017 | Hardemark | |
| 9,776,017 | B2 | 10/2017 | Flynn et al. | |
| 9,786,093 | B2 | 10/2017 | Svensson | |
| 9,795,806 | B2 | 10/2017 | Matsuzaki et al. | |
| 9,855,445 | B2* | 1/2018 | Mansfield | A61N 5/1067 |
| 9,884,206 | B2 | 2/2018 | Schulte et al. | |
| 9,931,522 | B2 | 4/2018 | Bharadwaj et al. | |
| 9,962,562 | B2 | 5/2018 | Fahrig et al. | |
| 9,974,977 | B2 | 5/2018 | Lachaine et al. | |
| 9,987,502 | B1 | 6/2018 | Gattiker et al. | |
| 10,007,961 | B2 | 6/2018 | Grudzinski et al. | |
| 10,071,264 | B2 | 9/2018 | Liger | |
| 10,092,774 | B1 | 10/2018 | Vanderstraten et al. | |
| 10,183,179 | B1 | 1/2019 | Smith et al. | |
| 10,206,871 | B2 | 2/2019 | Lin et al. | |
| 10,232,193 | B2 | 3/2019 | Iseki | |
| 10,258,810 | B2 | 4/2019 | Zwart et al. | |
| 10,279,196 | B2 | 5/2019 | West et al. | |
| 10,307,614 | B2 | 6/2019 | Schnarr | |
| 10,307,618 | B2* | 6/2019 | Mansfield | A61N 5/1049 |
| 10,315,047 | B2 | 6/2019 | Glimelius et al. | |
| 10,413,755 | B1 | 9/2019 | Sahadevan | |
| 10,525,285 | B1 | 1/2020 | Friedman | |
| 10,549,117 | B2 | 2/2020 | Vanderstraten et al. | |
| 10,603,514 | B2 | 3/2020 | Grittani et al. | |
| 10,609,806 | B2 | 3/2020 | Roecken et al. | |
| 10,661,100 | B2 | 5/2020 | Shen | |
| 10,702,716 | B2 | 7/2020 | Heese | |
| 2004/0000650 | A1 | 1/2004 | Yanagisawa et al. | |
| 2004/0104354 | A1 | 6/2004 | Haberer et al. | |
| 2005/0087700 | A1* | 4/2005 | Tadokoro | G21K 5/04 250/492.21 |
| 2006/0022152 | A1 | 2/2006 | Natori et al. | |
| 2006/0163496 | A1 | 7/2006 | Hiramoto et al. | |
| 2006/0226372 | A1* | 10/2006 | Yanagisawa | A61N 5/10 250/396 R |
| 2007/0034812 | A1 | 2/2007 | Ma et al. | |
| 2007/0164227 | A1 | 7/2007 | Yoshida | |
| 2007/0228291 | A1 | 10/2007 | Hiramoto et al. | |
| 2007/0252093 | A1* | 11/2007 | Fujimaki | A61N 5/1048 250/492.3 |
| 2008/0023644 | A1 | 1/2008 | Pedroni | |
| 2008/0067401 | A1 | 3/2008 | Harada | |
| 2009/0008575 | A1* | 1/2009 | Okazaki | A61N 5/10 250/492.1 |
| 2009/0283702 | A1* | 11/2009 | Umezawa | H05H 7/10 250/492.3 |
| 2010/0127184 | A1 | 5/2010 | Balakin | |

(56) References Cited

U.S. PATENT DOCUMENTS

| | | |
|---|---|---|
| 2010/0301235 A1 | 12/2010 | Bert et al. |
| 2011/0240874 A1* | 10/2011 | Iwata ............... A61N 5/1031 |
| | | 250/396 ML |
| 2012/0126135 A1 | 5/2012 | Illemann et al. |
| 2012/0264998 A1* | 10/2012 | Fujitaka ............ A61N 5/1043 |
| | | 600/1 |
| 2012/0280150 A1 | 11/2012 | Jongen |
| 2012/0313002 A1 | 12/2012 | Ikeda et al. |
| 2013/0087721 A1 | 4/2013 | Nishio et al. |
| 2013/0231516 A1 | 9/2013 | Loo et al. |
| 2014/0014851 A1* | 1/2014 | Asaba ................. H05H 7/12 |
| | | 250/396 R |
| 2014/0091734 A1 | 4/2014 | Gall et al. |
| 2014/0330066 A1* | 11/2014 | Fujii ................. A61N 5/1068 |
| | | 600/1 |
| 2016/0135765 A1* | 5/2016 | Vigdor ................ G01T 1/169 |
| | | 250/366 |
| 2017/0281981 A1* | 10/2017 | Mansfield ........... A61N 5/1043 |
| 2018/0133514 A1* | 5/2018 | Mansfield ........... A61N 5/1049 |
| 2019/0255361 A1* | 8/2019 | Mansfield ........... A61N 5/1067 |

FOREIGN PATENT DOCUMENTS

| | | |
|---|---|---|
| CN | 103794261 | 5/2014 |
| EP | 0826394 | 3/1998 |
| JP | H1151310 | 6/1999 |

OTHER PUBLICATIONS

Ultrahigh dose-rate FLASH irradiation increases the differential response between normal and tumor tissue in mice Favaudon, et al. Supplemental Materials, www.sciencetranslationalmedicine.org/cgi/content/full/6/245/245ra93/DC1 Published Jul. 16, 2014.

Design, Otpimisation and Monte Carlo Simulation of a 3D Range-Modulator for Scanned Particle Therapy; PTCOG 55 Annual Conference; May 22-28, 2016.

* cited by examiner

RADIATION THERAPY SYSTEMS AND METHODS

REFERENCE TO RELATED U.S. APPLICATIONS

This application is a continuation of the application with Ser. No. 15/850,472, now U.S. Pat. No. 10,307,618, entitled "Radiation Therapy Systems and Methods," by S. Mansfield, filed Dec. 21, 2017, which is a continuation of the application with Ser. No. 15/089,330, now U.S. Pat. No. 9,855,445, entitled "Radiation Therapy Systems and Methods," by S. Mansfield, filed Apr. 1, 2016, both of which are hereby incorporated by reference in their entirety. This application is related to the U.S. application with Ser. No. 15/087,292, entitled "Adaptive Pencil Beam Scanning," by J. Wulff, filed Mar. 31, 2016, and hereby incorporated by reference in its entirety.

BACKGROUND

The use of radiation therapy to treat cancer is well known. Radiation therapy (radiotherapy) involves directing a beam of high energy particles such as electrons, protons, or heavy ions into a target volume (e.g., a tumor or lesion) in a patient.

Before the patient is treated with radiation, a treatment plan specific to that patient is developed. The plan defines various aspects of the radiotherapy using simulations and optimizations based on past experiences. For example, for intensity modulated particle therapy (IMPT), the plan can specify the appropriate beam type and the appropriate beam energy. Other parts of the plan can specify, for example, the angle of the beam relative to the patient/target volume, the beam shape, and the like. In general, the purpose of the treatment plan is to deliver sufficient radiation to the target volume while minimizing the exposure of surrounding healthy tissue to radiation.

Existing IMPT dose delivery techniques utilize raster scanning that takes advantage of the well-known Bragg peak characteristic of a mono-energetic particle (e.g., proton) beam. By scanning the beam in the X and Y directions, a "layer" of dose can be "painted" within the target volume. Subsequent layers are painted in overlapping raster scan patterns using particles with a different energy that would thus stop at a different range (distance). Such scan patterns usually start at the most distal edge of the planning target volume and each subsequent layer is delivered, after a pause to change the beam energy, to a lesser range thus creating a Spread Out Bragg Peak (SOBP), until the final layer is delivered to the proximal edge of the planning target volume.

A fundamental concern during radiation therapy is that the target volume might move during dose delivery (e.g., due to the patient moving, breathing, etc.). Movement during dose delivery can inadvertently place healthy tissue in the path of the radiation intended for the target volume. Although it is theoretically possible for the raster scan pattern to track in-plane motion of the target volume, by superimposing the raster scan pattern with the instantaneous two-dimensional (X-Y) vector corresponding to that motion, any out-of-plane motions (particularly those of normal healthy structures proximal to the target) can introduce motion-related uncertainties that in turn can create dose overlaps ("hot spots") or, even worse, gaps ("cold spots") within the target volume.

A recent radiobiology study has demonstrated an advantageous effectiveness in sparing normal, healthy tissue from damage by delivering an entire, relatively high therapeutic radiation dose within a single short period of time (e.g., less than one second). However, in conventional raster-scanned IMPT, because dose delivery along each ray passing through the patient occurs successively at different points in time in the scan pattern and is thus spread out over time, the unavoidable dose that is delivered to the normal healthy structures is also spread out over time. Therefore, the radiobiological tissue-sparing effects reported in the aforementioned study are not realized using existing IMPT techniques.

Furthermore, contemporary radiation therapy delivery systems include dipole electromagnets and scanning magnets. The dipole magnets (often referred to as "bending magnets") direct (e.g., bend) the particle beam in a direction toward a nozzle, and the scanning magnets steer (deflect or scan) the beam in the X and Y directions. The dipole magnets typically utilize massive ferromagnetic return paths and therefore have a much slower magnetic hysteresis relative to the scanning magnets. That is, it takes much longer to change (increase or decrease) the level of magnetism in the dipole bending magnets than it does to steer the beam using the scanning magnets during IMPT delivery. Also, the relative slowness of varying the magnetic fields of the dipole bending magnets is the primary reason that existing IMPT systems utilize a method of scanning dose one layer at a time. The time spent changing the magnetic strength of the dipole magnets in order to change the incident beam energy constitutes a significant portion of the time required to deliver an IMPT therapy dose. Considering the comfort of the patient, for example, shorter radiotherapy sessions are highly preferred. Thus, the reliance on magnets, particularly the use of the dipole bending magnets, for adjusting particle beams is an obstacle to realizing the benefits of using relatively high therapeutic radiation doses within a very short period of time for dose delivery in radiotherapy.

SUMMARY

In an embodiment according to the present disclosure, a radiation therapy system includes an accelerator and beam transport system and a nozzle that can be aimed toward an object. The nozzle includes at least one scanning magnet that guides (e.g., steers, deflects, or scans) the beam toward various locations within a target volume within the object. The nozzle also includes a beam energy adjuster configured to adjust the beam by, for example, placing different thicknesses of material in the path of the beam to affect the energies of the particles in the beam. The beam energy adjuster may include one or both of a range shifter and a range modulator. In an embodiment, the range shifter is configured to place different thicknesses of material in the path of the beam to affect the distance that the particles penetrate into the object. In an embodiment, the range modulator is configured to place different thicknesses of material in the path of the beam to decrease the energies of at least a portion of the particles by varying the exiting beam particle energy over time, to spread out the Bragg peak.

Significantly, the range shifter and/or range modulator, placed in the nozzle as described in this disclosure, are "dynamically variable" (e.g., faster acting than the dipole magnets in the beam transport system). Consequently, a nozzle according to the present disclosure is capable of quickly adjusting the particles in the beam to create a scanned beam (as opposed to a scattered beam) that delivers an entire, relatively high therapeutic radiation dose in the target volume. For example, a dose of four grays can be delivered along a specified beam direction (e.g., a given ray) in less than one second.

Each ray is a part of a scan pattern and irradiates tissue along a different line segment through the target volume (a "target line segment"). A high dose that can be delivered in a short period of time along a target line segment may be referred to herein as a "shot." In an embodiment, a shot can be adjusted in energy (intensity) or range and delivered to the target volume with a Spread Out Bragg Peak (SOBP) that provides a uniform and otherwise suitably modified dose to an entire target line segment.

The intensity of the dose delivered in a shot can be adjusted to match the prescribed dose for a particular target line segment. Shots can be delivered using, for example, a predefined scanning pattern to irradiate different target line segments: a first adjusted beam that delivers a first dose with a SOBP along a first target line segment in a target volume can be created, and a second adjusted beam that delivers a second dose with a second SOBP along a second target line segment in the target volume can be created, where the second target line segment is displaced from the first target line segment. Each shot can be triggered in time and/or aimed in position to coincide with the position of a moving target within a patient based on, for example, a motion tracking system. Subsequent shots can be independently adjusted in intensity, in range, and with a suitable SOBP, and can also be triggered or aimed to coincide with the 4D (three dimensions plus time) position of each target line segment in the scan pattern until the entire target volume has been irradiated to the prescribed dose.

In an embodiment, a range shifter is in the nozzle, downstream of the scanning magnet(s). In another embodiment, the range shifter is in the nozzle, upstream of the scanning magnet(s). The range shifter provides a rapid means of quickly varying the range of the Bragg peak to match the distal edge of the planning target volume.

In an embodiment, the nozzle includes both a range modulator and a range shifter. The range modulator is downstream of the scanning magnet(s); the range shifter can be downstream or upstream of the scanning magnet(s). In an embodiment, the range modulator includes a number of arms extending from a hub. In an embodiment, each of the arms has a non-uniform thickness and a non-uniform width (and therefore a non-uniform amount of space between adjacent arms). The range modulator can rotate about the hub, so that the beam will pass through at least one of the arms and also can pass through the space between adjacent arms.

In an embodiment, the range modulator can be moved in a first direction (e.g., laterally, transverse to the path of the beam) so that it is either completely out of the path of the beam or is in the path of the beam. In an embodiment, the range modulator can also be moved in a second direction different from (e.g., perpendicular to) the first direction and transverse to the path of the beam.

The range modulator provides a means of quickly varying the energy in a scanned beam to create the desired extent of SOBP in a dynamically variable manner. By adjusting the position of the range modulator and rotating the range modulator, the beam can pass through different parts of at least one of its arms and therefore through different thicknesses of material and also through different amounts of space between adjacent arms, and therefore the extent of spread of the SOBP can be rapidly varied over a useful range.

The range modulator and/or the range shifter match the SOBP (distally and proximally) to the target volume (the planning target volume). Because the range modulator and the range shifter can achieve these effects quickly, a shot can advantageously be used for dose delivery. Thus, using shots, the entire target volume can be irradiated to the dose prescribed by the treatment plan while exposing healthy tissue to only a single, very short burst of radiation. Also, by delivering the entire dose within a short period of time, movement of the target volume becomes much less of an issue. Likewise, delivering a pattern of shots with varying intensity from a single beam direction quickly results in intensity-modulated radiation therapy delivery. Further, by delivering patterns of shots from multiple beam directions, a more refined intensity modulation can be achieved with lower dose delivered to healthy tissues. Importantly, because no dose is delivered distally to the Bragg peak, the dose delivered in this manner to any healthy tissue, outside the target volume, can thus be limited to a single very short burst of low dose radiation.

In summary, embodiments according to the present disclosure provide spatially and temporally precise, modulated irradiation of a moving target in a patient and take advantage of the tissue-sparing effects of the study mentioned above. Embodiments according to the present disclosure provide a more direct method for target volume scanning than the use of the conventional raster scanning technique described above. Each shot is aimed directly to coincide with the in-plane motion of the target using the scanning magnet(s), rather than having to distort the raster scan pattern. Aiming subsequent shots thusly avoids creating motion artifacts such as those caused by the interplay between the target motion of sequential raster scan patterns. Likewise, target motion in the distal-to-proximal direction can be compensated for by varying the range shifter accordingly between shots. Quality assurance is also made easier because the tracking and scanning processes are more independent of one another. Significantly, because a SOBP covering the entire length of each target line segment (from the distal edge to the proximal edge of the planning target volume) is delivered in a short burst, motion-induced uncertainties do not create gaps or overlaps (cold spots or hot spots) within the target volume.

These and other objects and advantages of the various embodiments of the present disclosure will be recognized by those of ordinary skill in the art after reading the following detailed description of the embodiments that are illustrated in the various drawing figures.

This summary is provided to introduce a selection of concepts in a simplified form that is further described below in the detailed description that follows. This summary is not intended to identify key features or essential features of the claimed subject matter, nor is it intended to be used to limit the scope of the claimed subject matter.

BRIEF DESCRIPTION OF DRAWINGS

The accompanying drawings, which are incorporated in and form a part of this specification and in which like numerals depict like elements, illustrate embodiments of the present disclosure and, together with the detailed description, serve to explain the principles of the disclosure.

DETAILED DESCRIPTION

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

A "ray" is a part of a scan pattern and irradiates tissues along a different line segment through the target volume (a "target line segment"). A high dose that can be delivered in a short period of time along a target line segment may be referred to herein as a "shot."

Figure 1:
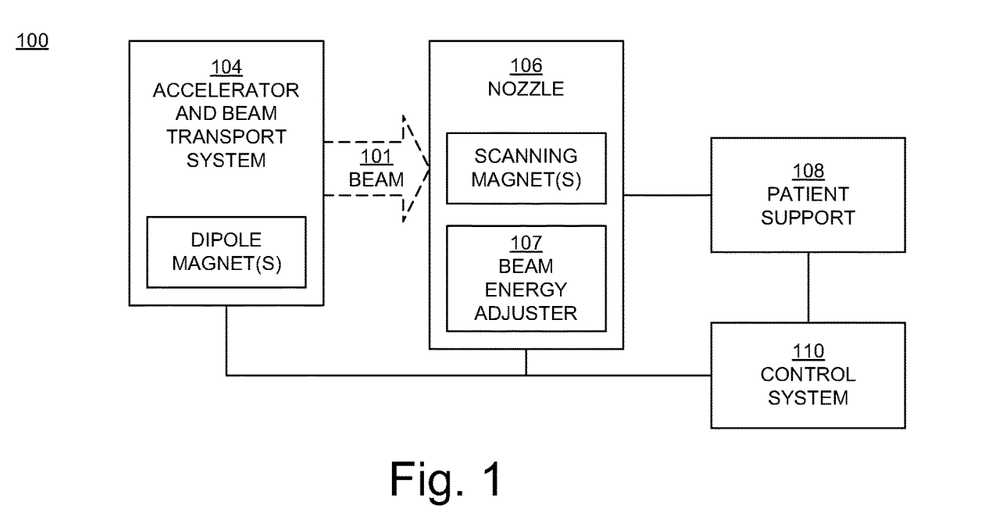
FIG. 1 is a block diagram showing selected components of a radiation therapy system upon which embodiments according to the present disclosure can be implemented.

FIG. 1 is a block diagram showing selected components of a radiation therapy system 100 upon which embodiments according to the present disclosure can be implemented. In the example of FIG. 1, the system 100 includes an accelerator and beam transport system 104 and a nozzle 106.

The accelerator and beam transport system 104 generates and accelerates a beam of charged particles, such as electrons, protons, and heavy ions, and contains the particles in a well-defined beam. In an embodiment, the accelerator is an isochronous cyclotron capable of continuous wave output. The accelerator (e.g., the cyclotron) extracts particles with a specified energy. This provides a high, continuous wave beam current for the high dose rate per shot. Other types of accelerators can be used, such as a pulsed proton accelerator such as a synchrocyclotron or a synchrotron. The accelerator (e.g., cyclotron) can be a lower power output cyclotron, such as a cyclotron that accelerates particles to the range of 70-300 MeV.

The accelerator and beam transport system 104 includes components (e.g., dipole magnets, also known as bending magnets) that direct (e.g., bend, steer, or guide) the beam through the accelerator and beam transport system in a direction toward and into the nozzle 106. The accelerator and beam transport system 104 may also include components that are used to adjust the beam energy entering the nozzle 106 so that it is different from the beam energy extracted from the accelerator. In an embodiment, sets of quadrupole magnets are located along the beam paths in the accelerator and beam transport system 104.

The nozzle 106 is used to aim the beam toward various locations within an object (e.g., a patient) supported on the supporting device 108 (e.g., a chair or table) in a treatment room. The nozzle 106 may be mounted on or a part of a gantry (not shown) so that it can be moved relative to the supporting device 108; the supporting device may also be moveable. In an embodiment, the accelerator and beam transport system 104 is also mounted on or is a part of the gantry; in another embodiment, the accelerator and beam transport system is separate from (but in communication with) the gantry.

A control system 110 receives and implements a prescribed treatment plan. In an embodiment, the control system 110 includes a computer system having a processor, memory, an input device (e.g., a keyboard), and perhaps a display in well-known fashion. The control system 110 can receive data regarding operation of the system 100. The control system 110 can control parameters of the accelerator and beam transport system 104, nozzle 106, and supporting device 108, including parameters such as the energy, intensity, direction, size, and/or shape of the beam, according to data it receives and according to the prescribed treatment plan.

As noted above, the particles entering the nozzle 106 have a specified energy. Thus, in embodiments according to the present disclosure, the nozzle 106 includes one or more components that affect (e.g., decrease, modulate) the energy of the particles in the beam. In an embodiment, the nozzle 106 also includes components (e.g., X-Y scanning magnets) that steer (e.g., guide, deflect, or scan) the beam particles in the X and Y directions, to scan a target volume in a patient on the supporting device 108.

The term "beam energy adjuster" is used herein as a general term for a component or components that affect the energy of the particles in the beam. In various embodiments, the beam energy adjuster 107 includes a range modulator, a range shifter, or both a range modulator and a range shifter. That is, when the term "beam energy adjuster" is used, then the element being discussed may be a range modulator, a range shifter, or both a range modulator and a range shifter. Note that, in an embodiment in which the beam energy adjuster includes both a range modulator and a range shifter, the range modulator and the range shifter may be separated from each other by other nozzle components. This is illustrated in further detail in FIGS. 2A, 2B, 2C, and 2D.

Figure 2A:
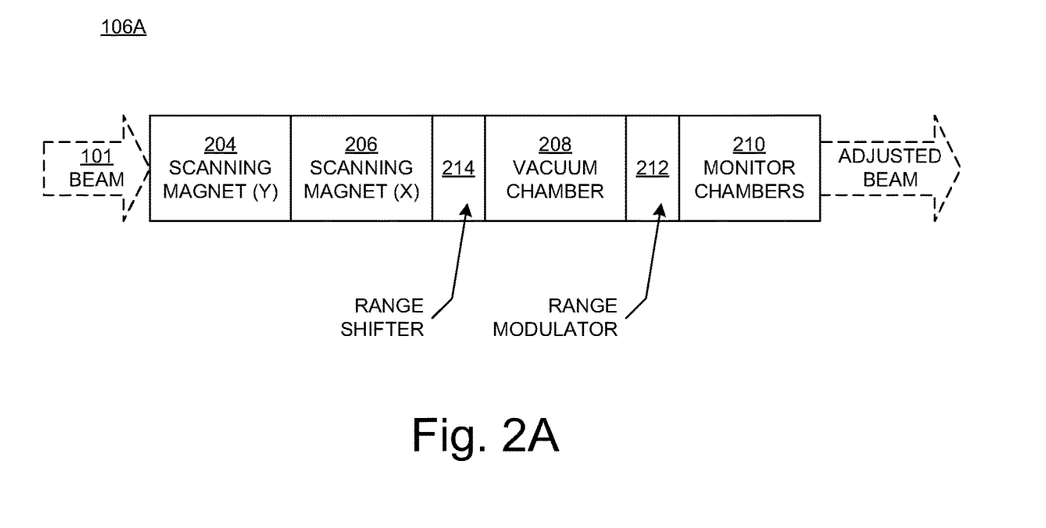
FIGS. 2A, 2B, 2C, and 2D are block diagrams illustrating selected components of a nozzle in embodiments according to the present disclosure.

FIG. 2A is a block diagram illustrating selected components of a nozzle 106A in an embodiment according to the present disclosure. The nozzle 106A receives a charged particle beam 101 from the accelerator and beam transport system 104 (FIG. 1). In the example of FIG. 2A, the nozzle 106A includes one or more scanning magnets that guide the beam 101. In an embodiment, the X-Y scanning magnets include a first (Y) magnet 204 and a second (X) magnet 206 for vertical and horizontal beam deflection to scan the beam across a planning target volume in an object (e.g., a patient). The Y-magnet 204 can be placed before or after the X-magnet 206 in the nozzle 106A.

In an embodiment, the nozzle 106A includes a vacuum chamber 208 and monitor chambers 210. The monitor chambers 210 monitor the radiation exiting from the vacuum chamber 208.

In the FIG. 2A embodiment, the nozzle 106A includes a range modulator 212 that is downstream of the X-Y scanning magnets 204 and 206. Thus, the range modulator 212 acts on a scanned particle beam (as opposed to a scattered particle beam). In an embodiment, the range modulator 212 is at the end of (outside of) the vacuum chamber, before the monitor chambers 210; the vacuum ends at the range modulator 212.

As noted above, the initial energies of the particles within the beam 101 are determined by the acceleration provided to the particles by the accelerator and beam transport system 104 (FIG. 1). The range modulator 212 varies (modulates) the energies of a portion of the particles in the scanned beam. More specifically, the range modulator 212 decreases the energy of a portion of the individual particles (e.g., by varying the exiting beam particle energy over time), thereby increasing the energy distribution of the scanned particle beam and spreading the dose distribution along the direction of travel of the scanned particle beam to deliver a dose with a Spread Out Bragg Peak (SOBP) to a target line segment (FIG. 3) in a target volume in an object (e.g., a patient).

Continuing with reference to FIG. 2A, as noted above, the range modulator 212 is located downstream of the X-Y scanning magnets 204 and 206. This avoids creating rapidly varying beam energy within the fixed or slowly varying magnetic field of the X-Y scanning magnets. This also avoids causing the beam to spread, as lower energy particles are bent more tightly than higher energy particles.

The range modulator 212 rapidly varies the exiting beam particle energy to create the desired extent of SOPB in a dynamic manner. Also, the range modulator 212 is moveable, so that it can be moved into and out of the beam path and to change the thickness of material exposed to the beam, thereby also changing the extent of the SOBP. This is further discussed below in conjunction with FIGS. 4A-4D. As will be seen by that discussion, the range modulator 212 is configured so that the extent of spread of the SOBP can be rapidly varied over a useful range in a beam that is separately being scanned in both the X and Y directions.

In the embodiment of FIG. 2A, the nozzle 106A also includes a range shifter 214. This is in contrast to a conventional radiation therapy (e.g., proton) system in which a degrader (range shifter) is located after the accelerator and before the gantry entry point. In the FIG. 2A embodiment, the range shifter 214 is in the nozzle 106A and downstream of the X-Y scanning magnets 204 and 206 and upstream of the range modulator 212. That is, the range shifter 214 is in the nozzle 106A and between the range modulator 212 and the X-Y scanning magnets 204 and 206.

The range shifter 214 is configured to change (e.g., decrease) the energies of the particles in the particle beam to affect the distance that the particles penetrate into the target volume; the range shifter affects the range of the beam. More specifically, the range shifter 214 provides a rapid means of varying the range of the Bragg peak so that the Bragg peak occurs at the distal edge of the planning target volume for each shot. An embodiment of the range shifter 214 is described further below in conjunction with FIG. 5.

In the FIG. 2A embodiment, the range modulator 212 and the range shifter 214 constitute the beam energy adjuster 107 (FIG. 1). Effectively, the range modulator 212 and the range shifter 214 each affect or adjust the beam, but in different ways: the range shifter is used for changing (e.g., decreasing) the beam energy to control the range (penetration) of the beam, and the range modulator is used for spreading out the Bragg peak.

Figure 2B:
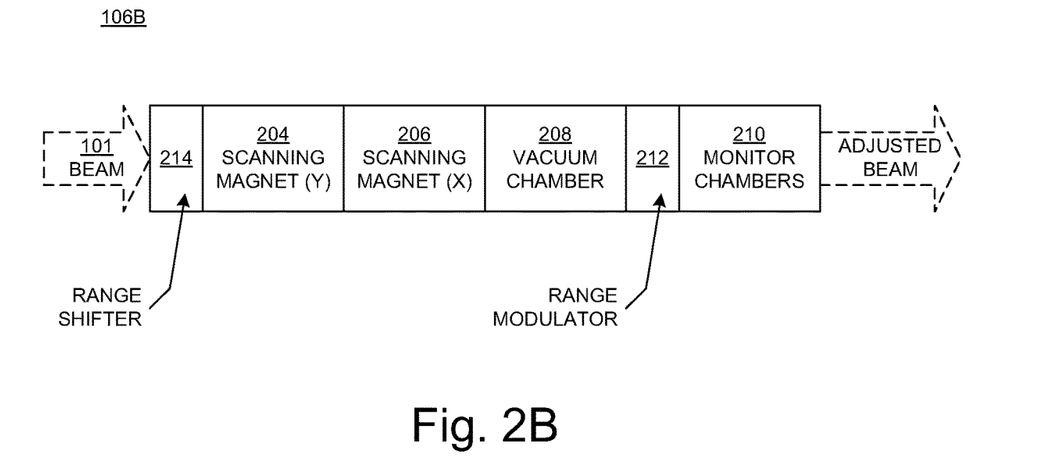

FIG. 2B is a block diagram illustrating selected components of a nozzle 106B in another embodiment according to the present disclosure. In contrast with the nozzle 106A of FIG. 2A, the range shifter 214 in the nozzle 106B is located upstream of the X-Y scanning magnets 204 and 206, between the X-Y scanning magnets and the accelerator and beam transport system 104 (FIG. 1). Locating the range shifter 214 upstream of the X-Y scanning magnets 204 and 206 means that the particle beam does not have to be compensated for the effect of the scanning magnets on the beam. In the FIG. 2B embodiment, the range modulator 212 and the range shifter 214 constitute the beam energy adjuster 107 (FIG. 1).

Figure 2C:
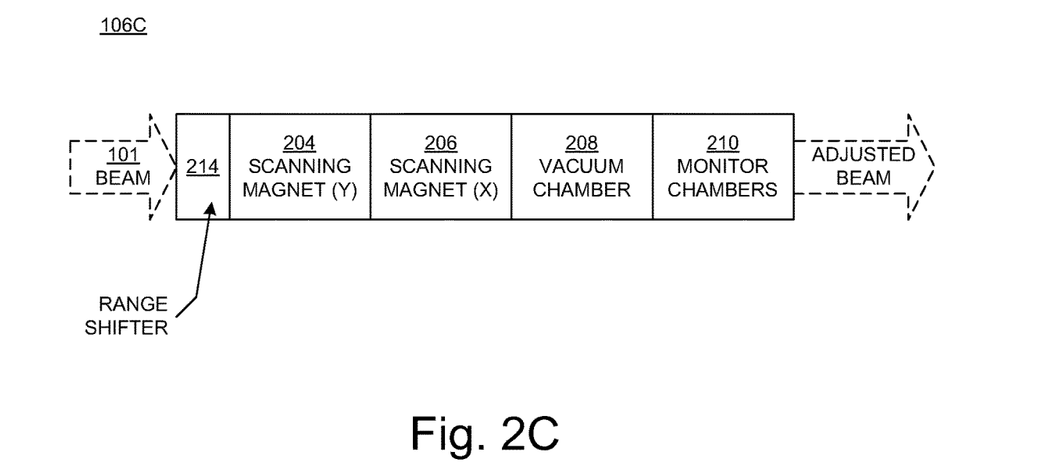

FIG. 2C is a block diagram illustrating selected components of a nozzle 106C in another embodiment according to the present disclosure. In contrast with the nozzles 106A and 106B of FIGS. 2A and 2B, respectively, the nozzle 106C includes the range shifter 214 upstream of the X-Y scanning magnets 204 and 206, between the X-Y scanning magnets and the accelerator and beam transport system 104 (FIG. 1), but does not include a range modulator. In the FIG. 2C embodiment, the range shifter 214 constitutes the beam energy adjuster 107 (FIG. 1).

Figure 2D:
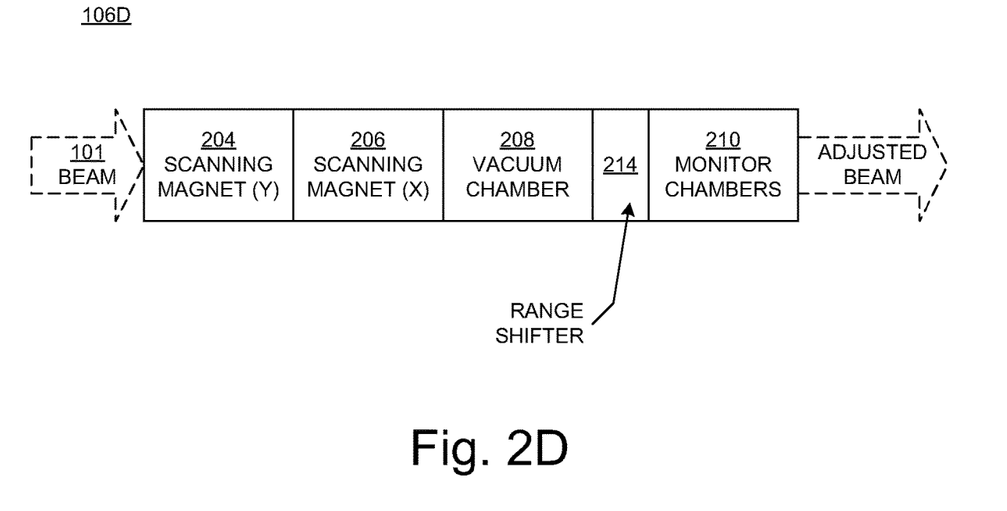

FIG. 2D is a block diagram illustrating selected components of a nozzle 106D in another embodiment according to the present disclosure. Like the nozzle 106C of FIG. 2C, the nozzle 106D includes the range shifter 214 but not a range modulator. In contrast to the FIG. 2C embodiment, the range shifter 214 is downstream of the X-Y scanning magnets 204 and 206. In the FIG. 2D embodiment, the range shifter 214 constitutes the beam energy adjuster 107 (FIG. 1).

Figure 3:
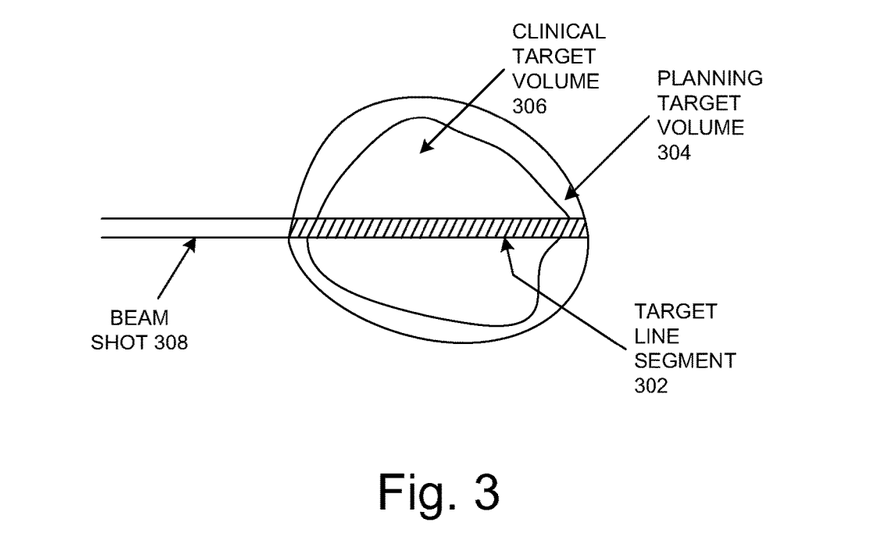
FIG. 3 illustrates an example of dose delivery along a target line segment in a planning target volume in an embodiment according to the present disclosure.

FIG. 3 illustrates an example of a target line segment 302 in a planning target volume 304. The planning target volume refers to the size of the volume to be irradiated, and encompasses the clinical target volume 306, which refers to size of the actual tumor to be treated. In the example of FIG. 3, a particle beam (shot) 308 is traveling in the direction from left to right. In the orientation of FIG. 3, the edge at the right-hand side of the planning target volume 304 (the edge furthest from the direction of the incident particle beam 308) is referred to as the distal edge, and the edge at the left-hand side of the planning target volume (the edge nearest the direction of the incident particle beam) is referred to as the proximal edge. In embodiments according to the present disclosure, the SOBP delivers a uniform dose in the direction along the target line segment 302 from the proximal edge to the distal edge.

Figure 4A:
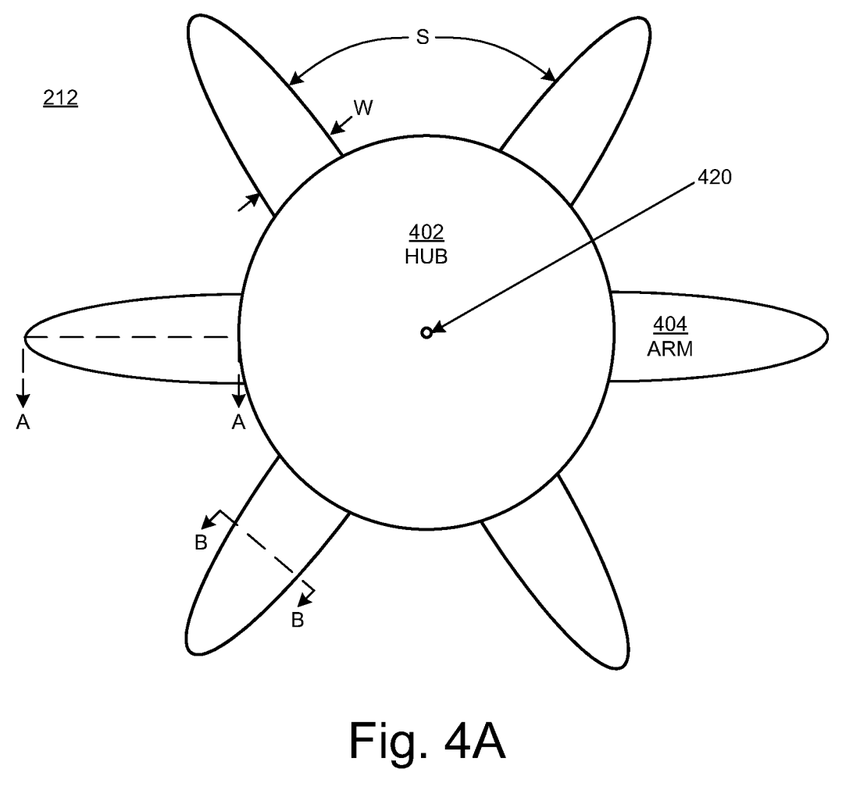
FIG. 4A illustrates a frontal view of a range modulator in an embodiment in accordance with the present disclosure.

FIG. 4A illustrates a frontal view (viewed from the perspective of the incident particle beam) of the range modulator 212 in an embodiment in accordance with the present disclosure. In this embodiment, the range modulator 212 is configured to place different thicknesses of material (including zero thickness; that is, no material) in the path of the scanned beam to vary the energy of the particles as described above. More specifically, in an embodiment, the range modulator 212 includes a number of arms 404 or blades extending from a hub 402. However, the range modulator 212 can be implemented using a single arm. In an embodiment, the arms 404 of the range modulator 212 are each made of the same material (e.g., graphite). In another embodiment, the arms 404 are made of different materials; that is, one arm may be made of one material or combination of materials, and another arm may be made of a different material or materials.

Each of the arms 404 has a non-uniform thickness. In an embodiment, the thicknesses of the arms 404 decrease as the distance from the hub increases.

In an embodiment, the lengths of the chords of the arms 404 decrease as the distance from the hub 402 increases; that is, the widths of the arms decrease as the distance from the hub increases (where width, W, is the dimension facing the incident particle beam). Thus, in an embodiment, the amount of space, S, between the arms 404 increases as the distance from the hub 402 increases. While the arms 404 are illustrated as being semi-elliptical in shape, the present disclosure is not so limited; the arms may be more rectangular in shape, with rounded corners, for example. Generally speaking, the shapes of the arms 404 can be optimized to achieve design objectives with regard to, for example, selecting and controlling the extent of the SOBP.

The range modulator 212 can rotate clockwise and/or counter-clockwise about an axis 420 through the center of the hub 402 in order to place the arms 404 (one arm at a time) into the path of the scanned beam (into the beam line). The range modulator 212 can also rotate to a position that allows the beam to pass through the space between two adjacent arms. The range modulator 212 can rotate continuously to allow the beam to pass through a varying thickness/width of a combination of at least one arm and at least one amount of space; the varying material thickness due to that rotation creates a desired SOBP. As will be described further below, the range modulator 212 can be moved in the horizontal direction so that the incident particle beam will pass through a different part of an arm and hence through a different thickness and width of material and also through a different amount of space when the range modulator is rotated. The range modulator 212 can also be moved to a position so that it is entirely outside of the beam. In an embodiment, the range modulator 212 can also be moved in the vertical direction, allowing the range modulator to be placed virtually anywhere in or out of the beam.

Figure 4B:
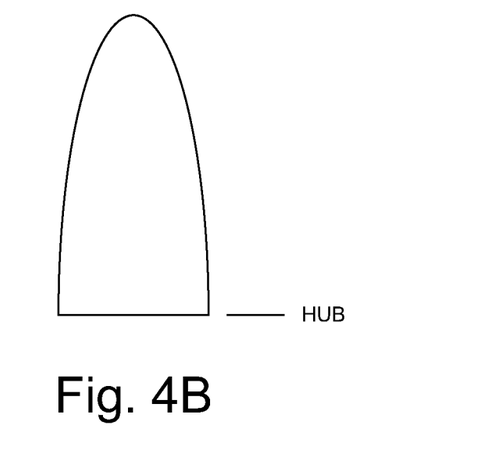
FIGS. 4B and 4C illustrate cross-sectional views of an arm of a range modulator in an embodiment according to the present disclosure.

FIG. 4B illustrates a cross-sectional view of an arm 404 along the cut-line A-A of FIG. 4A in an embodiment according to the present disclosure. In the embodiment of FIG. 4B, the thickness of the arm 404 decreases as the distance from the hub 402 increases. That is, the arm 404 is thickest where it meets the hub 402 and thinnest at its tip.

Figure 4C:
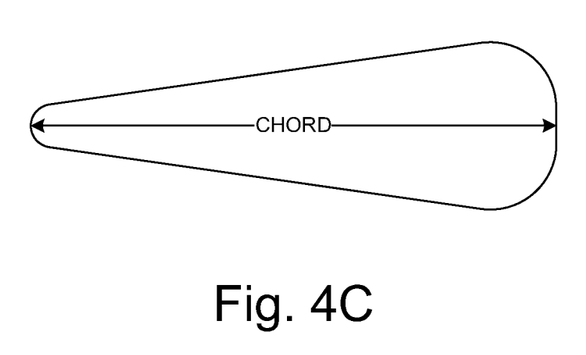

FIG. 4C illustrates a cross-sectional view of an arm 404 along the cut-line B-B of FIG. 4A in an embodiment according to the present disclosure. In the embodiment of FIG. 4C, the thickness of the arm 404 changes along its chord. That is, the arm 404 is thickest at one of its edges and thinnest at its other edge.

The shape (profile and cross-sections) of the arms 404 is not limited to the examples of FIGS. 4B and 4C.

Figure 4D:
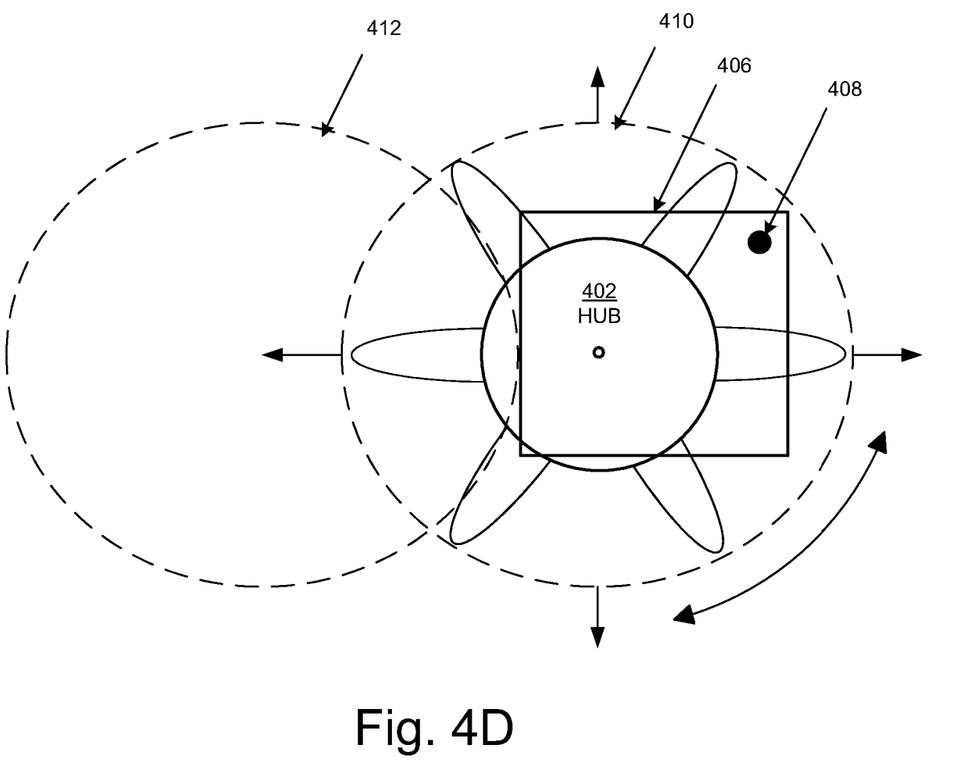
FIG. 4D illustrates positioning of a range modulator in an embodiment according to the present disclosure.

With reference to FIG. 4D, in an embodiment, the range modulator 212 can be moved in a first direction (e.g., transverse to the path of the beam) so that it is completely out of the path of the beam or is in the path of the beam. In an embodiment, the range modulator 212 can also be moved in a second direction that is different from (e.g., perpendicular to) the first direction and transverse to the path of the beam. In other words, in an embodiment, the range modulator 212 can be moved in only one direction (e.g., horizontally); and in another embodiment, the range modulator can be moved both horizontally and vertically (and hence diagonally). In an embodiment in which the range modulator 212 can move in only one direction, the diameter of the hub 402 can be sized so that it is equivalent or nearly equivalent to the maximum lateral beam scanning field width at the elevation of the hub.

Any of a number of different mechanisms can be used to move the range modulator 212 horizontally and/or vertically. For example, the range modulator 212 can be mounted on a sliding stage or assembly that allows it to be moved in either or both directions, depending on the embodiment.

In FIG. 4D, the maximum beam scanning field size is represented by a box 406, and the path of the particle beam (a beam shot) is represented by a darkened circle 408 within the box. The range modulator 212 can be positioned corresponding to the scan position of the particle beam within the maximum beam scanning field size 406, as deflected by the scanning magnets 204 and 205. For example, if the range modulator 212 is in the position indicated by the dashed circle 410, then the beam will pass through a particular thickness of one of the arms 404; if the range modulator is then moved to the right, the beam will pass through a thicker part of one of the arms; if the range modulator is instead moved to the left, the beam will pass through a thinner part of one of the arms. If the range modulator 212 is in the position indicated by the dashed circle 412, for example, then it is out of the way of any beam path. As mentioned above, the range modulator 212 can be rotating continuously while it is in position in order to create a desired SOBP; by moving the range modulator transversely (horizontally and/or vertically) to a different position, the extent of the SOBP is selected and controlled.

When the range modulator 212 is rotating in the beam path, the beam passes through at least one of the arms 404 and at least one space between adjacent arms. The speed of rotation of the range modulator 212 can be varied such that a beam shot passes through more than one arm 404 and more than one space between adjacent arms. The rotation speed of the range modulator 212 can also be adjusted so that it is synchronized with the operation of the accelerator. Any of a number of different mechanisms can be used to rotate the range modulator 212. For example, the range modulator 212 can be driven directly or indirectly by a motor connected to the hub 402.

In an embodiment, when the range modulator 212 is rotating in the beam path, the position of the range modulator in the beam path is chosen (and the range modulator is moved to that position) so that the varying material thickness due to the varying thicknesses/widths of the arms 404 and the amount of space between the arms results in the desired SOBP. At any point in time, the Bragg peak is a function of the radial distance of the beam from the hub 402. The extent of SOBP can be varied continuously from having no particle beam impingement and thus no SOBP (a pristine Bragg peak) when the beam is beyond the tip of one of the arms 404 (such as the position indicated by the dashed circle 412), to creating a maximum SOBP when the beam passes through the thickest part of one of the arms, for example, near the hub 402. The desired extent of SOBP can be achieved by moving the range modulator 212 so that the beam passes through the range modulator at a radial distance from the hub 402 corresponding to the desired SOBP. By moving the range modulator 212 rotationally and/or radially (in a horizontal and/or vertical direction), any desired SOBP can be achieved.

The range modulator 212 can be quickly positioned (rotationally and radially) and thus can be used to quickly change the SOBP, much more quickly than could be achieved using magnets. Consequently, a dose of four grays can be delivered along a target line segment in less than one second. Moreover, a dose of at least 20 grays can be delivered along a target line segment in less than 500 milliseconds.

Figure 5:
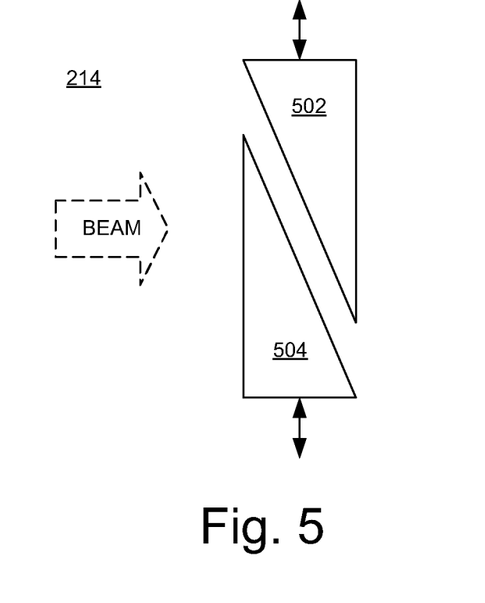
FIG. 5 illustrates a range shifter in an embodiment according to the present disclosure.

FIG. 5 illustrates a range shifter 214 in an embodiment according to the present disclosure. In this embodiment, the range shifter 214 includes a pair of wedges 502 and 504. In an embodiment, the wedges 502 and 504 are made of graphite. The wedges 502 and 504 can be moved in opposite directions to present a uniform but variable cross-sectional thickness to a particle beam passing through the wedges.

In an embodiment, the wedges 502 and 504 can be rapidly adjusted, moving along a programmed motion profile. When placed downstream of the X-Y scanning magnets 204 and 206 (FIG. 6), the wedges 502 and 504 can act as a range modulator to create a desired SOBP extent in a dynamically variable manner.

The range shifter 214 is not limited to the embodiment of FIG. 5. The range shifter 214 can be implemented in many different ways to achieve its function of creating a desired and dynamic SOBP.

For example, the wedges 502 and 504 may be made of the same material or combination of materials, or the wedges may be made of different materials or combinations of material; that is, one wedge may be made of one material or combination of materials, and another wedge may be made of a different material or materials. The materials may have different densities. Accordingly, the range shifter 214 may be made with components that are other than wedge-shaped. For example, the components may be block-shaped. The density of each block may be non-uniform such that an incident beam will pass through different densities of material depending on where and how the blocks are placed in the path of the beam and where and how the blocks are placed relative to one another. Also, different densities and thicknesses of material can be used; for example, wedge-shaped components that also have non-uniform densities can be used. The range shifter 214 can be implemented using more than two components (e.g., more than two wedges or blocks).

As mentioned above, in an embodiment, an isochronous cyclotron capable of continuous wave output can be used to generate a particle beam. In an embodiment, movement (e.g., rotational, radial, lateral) of the range modulator 212 can be synchronized with the beam source or generator (e.g., with the isochronous cyclotron). For example, sensors can be used to monitor the speed, position, and phase of the range modulator 212 and that information can be used (e.g., by the control system 110) to synchronize the movement of the range modulator to compensate for variations in the intensity of the beam output by the isochronous cyclotron or to compensate for effects of the X-Y scanning magnets 204 and 206. Then, the range shifter 214 is used to "trim" the distal edge of the planning target volume, thus reducing scatter.

Figure 6:
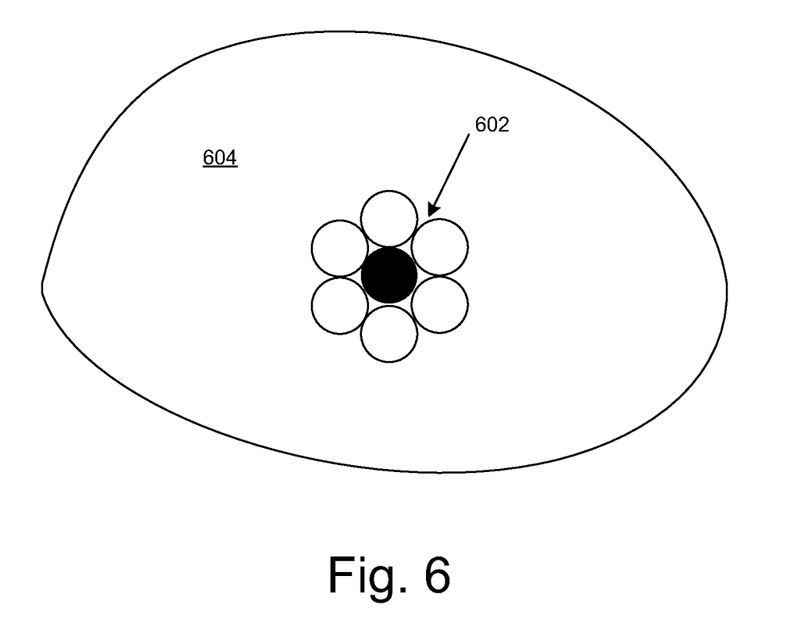
FIG. 6 illustrates a number of spots that represent the intersection of an incident particle beam with a layer of a planning target volume in an embodiment according to the present disclosure.

FIG. 6 illustrates a number of spots 602 that represent the intersection of an incident particle beam with a layer 604 of a target volume in an embodiment according to the present disclosure. In an embodiment, a variable spot size feature is incorporated by varying the current (and therefore the field strength) in focusing magnets, such as sets of quadrupole magnets located along the beam paths in the accelerator and beam transport system 104 (FIG. 1). By varying the spot size, the volume of a cylinder of targeted tissue that is exposed to radiation along a target line segment can be varied, with a corresponding inverse change in the dose rate for a given beam current. Such a capability is useful in improving the coverage and speed of dose delivery to a variety of target volume sizes and shapes. For example, a larger spot size could be useful in painting a dose over larger areas, particularly if the desired dose is not too high, while a smaller spot size may be useful in contouring a complex shape. A scan pattern can utilize staggered spots that are arranged similar to a hexagonal grid as shown in FIG. 6. The particle scatter normally encountered in a SOBP will naturally provide a penumbra region surrounding the cylinder around each target line segment. This unavoidable penumbra is useful in maintaining dose uniformity to target tissues that lie between shots. A planned extent of overlap between adjacent shots can be used to assure adequate target coverage in the "gaps" between adjacent spots of the hexagonal grid. Alternatively, a pattern of larger spots can be interleaved together with smaller spots to fill in any gaps. The extent of particle scatter and therefore the cross-sectional diameter of significant radiation dose coverage greatly increases in the region of the SOBP (e.g., within the target volume) in comparison to the region along the proximal beam (passing through healthy, normal tissue). Therefore, a significant degree of overlap of dose within the target volume from adjacent shots can be accommodated without creating a dose overlap in the normal tissue that the beam passes through. Accordingly, the positive radiobiological effects attributable to the use of shots as described herein can be preserved.

Figure 7:
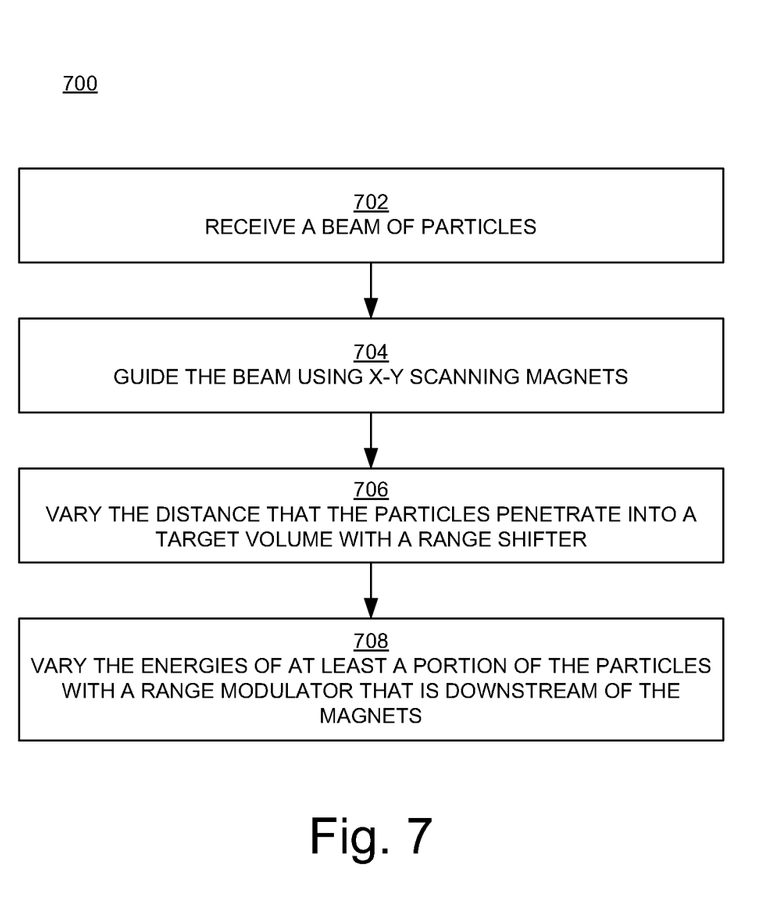
FIG. 7 is a flowchart of a radiation therapy method in an embodiment according to the present disclosure.

FIG. 7 is a flowchart 700 of a radiation therapy method in an embodiment according to the present disclosure. Although steps and sequencing thereof are disclosed in FIG. 7 describing the operations of this method, such steps and sequencing are examples. Embodiments are well suited to performing various other steps or variations of the steps recited in the flowchart 700, and in a sequence other than that depicted and described herein.

In block 702, a beam of particles is received into a nozzle.

In block 704, the beam is scanned (raster scanned) using a number of X-Y scanning magnets.

In block 706, in an embodiment, the distance that the particles penetrate into a target volume is adjusted with a range shifter that is configured to place different thicknesses of material in the path of the beam. In an embodiment, the range shifter is in the nozzle, downstream of the scanning magnets and can act as a range modulator; in another embodiment, the range shifter is in the nozzle, upstream of the scanning magnets.

In block 708, in an embodiment, the energies of at least a portion of the particles in the beam are also adjusted with a range modulator that is in the nozzle and downstream of the scanning magnets (thus the range modulator is exposed to a scanned beam).

Thus, the nozzle can be used to create an adjusted beam that delivers a dose with a SOBP along a target line segment (a shot) in a target volume aligned with the nozzle. The intensity of the dose delivered in a shot can be adjusted to match the prescribed dose for a particular target line segment. Shots can be delivered using, for example, a predefined scanning pattern to irradiate different target line segments; a first adjusted beam that delivers a first dose with a SOBP along a first target line segment in a target volume can be created, and a second adjusted beam that delivers a second dose with a second SOBP along a second target line segment in the target volume can be created, where the second target line segment is displaced from the first target line segment.

The range shifter and/or range modulator placed in the nozzle as described in this disclosure are dynamically variable (e.g., faster acting than the dipole bending magnets in the beam transport system). In an embodiment, the dose delivered along the target line segment is at least four grays and is delivered in less than one second. In another embodiment, the dose delivered along the target line segment is at least 20 grays and is delivered in less than 500 milliseconds.

In an embodiment, treatment planning and dose delivery are performed using multiple beams from different directions and nozzles, instead of using a single nozzle as described above. Each beam can be delivered at a separate time with obtuse or large acute angles between each direction. Because of the fundamental property of a particle beam in which no dose is delivered distally to the Bragg peak, no normal, healthy tissue along a ray beyond that point will receive an unwanted dose. Also, the proximal portions of any rays aimed from different beam directions do not overlap each other for directions that have an obtuse angle relative to each other. Even for beam directions at large acute angles, the extent of overlap is small. Any such overlap outside the target would reduce the positive effects attributable to the use of shots as described herein, so it is desirable to minimize any overlap.

Multiple beam directions are beneficial for at least two reasons. First, scanning dose through the target from multiple directions will greatly reduce the extent and magnitude of any dose inhomogeneity caused by the scan pattern or motion-induced range uncertainty from any one direction, as any of these effects (if present) would be overlapped within the target volume from separate directions. Second, scanning from multiple directions provides significantly greater independent degrees of freedom that can be utilized in treatment plan optimization while also significantly reducing the dose level to any normal, healthy tissue; the entrance dose is spread out over a larger volume of normal tissue.

Two nozzles, each as described above, can be placed coaxially and opposite each other with both aimed at the isocenter. A fast "kicker" magnet in a fixed beam would direct the beam back-and-forth between separate gantry-mounted paths feeding each nozzle. Scanning within each nozzle would be such that beams from both nozzles would both strike the same tissue sequentially or otherwise as close to each other in time as practical (e.g., within one second or within 500 milliseconds of each other), thus taking advantage of the positive radiobiological effects attributable to the use of shots as described herein. Because the planning target volume is typically not at the precise center of the patient, a range shifter such as the range shifter 214 described above can be employed in each nozzle to bring the SOBP from both nozzles into spatial coincidence. Because a very similar SOBP is delivered to the same target line segment from both directions, the magnitude of dose delivered to any normal, healthy tissue along the same line (proximal to the target from each direction) is reduced by half. Another advantage is that this arrangement of nozzles allows a treatment planner to independently optimize the shape and intensity of the scan pattern delivered from each direction to beneficially trade off different dose objectives or constraints during planning. For example, paired nozzles can be used to limit the dose to a specific organ-at-risk that is partially overlapping the planning target volume. No dose is delivered distally to the target beyond the Bragg peak, and this characteristic can be taken advantage of during treatment planning, especially when proton beams are to be used.

Fixed beams can also be employed rather than gantry-mounted beams, either singly or as an opposed pair as described above. The inability to preferentially aim the beam in an ideal direction is offset by a significantly lower capital expenditure. Some disease sites may not require a rotating gantry in order to be effectively treated with IMPT. For example, a pair of fixed nozzles placed in a vertical plane can be arranged to simultaneously deliver an AP/PA (anteroposterior/posteranterior) pair of opposing beams to treat a lung tumor. Similarly, a bilateral beam arrangement with opposing nozzles in a horizontal plane may be useful for other disease sites such as sites in the head and neck.

Other relative beam orientations in a multiple nozzle system (such as orthogonal) could be used, or additional nozzle beam lines and nozzles could be added (e.g., to implement three or four beam directions simultaneously).

In summary, embodiments according to the present disclosure provide spatially and temporally precise, modulated irradiation of a moving target in a patient and take advantage of the tissue-sparing effects of the study mentioned above. Embodiments according to the present disclosure provide a more direct method for target volume scanning than the use of the conventional raster scanning technique described above. Each shot is aimed directly to coincide with the in-plane motion of the target using the X-Y scanning magnets, rather than having to distort the raster scan pattern. Quality assurance is also made easier because the tracking and scanning processes are more independent of one another. Significantly, because a SOBP covering the entire length of each target line segment (from the distal edge to the proximal edge of the planning target volume) is delivered in a short burst, motion-induced uncertainties do not create gaps or overlaps (cold spots or hot spots) within the target volume.

Embodiments according to the present invention can be used to with types of external beam radiotherapy other than IMPT such as, for example, intensity modulated radiation therapy (IMRT), image-guided radiotherapy (IGRT), RapidArc™ radiotherapy, stereotactic body radiotherapy (SBRT), and stereotactic ablative radiotherapy (SABR). Embodiments according to the present disclosure can be incorporated into methods and systems used for planning radiotherapy treatments based on IMPT and other types of radiotherapy. A shot—a high dose that can be delivered in a short period of time along a target line segment—can be adjusted in energy (intensity) or range and delivered to the target volume with a SOBP that provides a uniform and otherwise suitably modified dose to an entire target line segment. The intensity of the dose delivered in a shot can be adjusted to match the prescribed dose for a particular target line segment. Subsequent shots can be independently adjusted in intensity, in range, and with a suitable SOBP, and can also be triggered or aimed to coincide with the 4D (three dimensions plus time) position of each target line segment in the scan pattern until the entire target volume has been irradiated to the prescribed dose. Radiotherapy treatments can be improved by taking advantage of this capability to quickly and accurately vary energy and range on the fly (dynamically). Treatment planning can also be improved because planners are presented with the capability to precisely control dose delivery.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:
1. A radiation therapy method, comprising:
generating a beam of particles with an accelerator and beam transport system comprising focusing magnets along the path of the beam;

aiming the beam toward a target volume with a nozzle comprising scanning magnets that steer the beam toward different locations within the target volume;

adjusting the beam in the nozzle by affecting energies of the particles in the beam with a beam energy adjuster in the nozzle; and varying current to vary field strength of the focusing magnets to vary sizes of spots where the beam intersects the different locations in the target volume.

2. The radiation therapy method of claim 1, wherein said adjusting the beam comprises placing different thicknesses of material of a range shifter in the nozzle in the path of the beam to affect the distance that the particles penetrate into the target volume and position a Spread Out Bragg Peak within the target volume.

3. The radiation therapy method of claim 2, wherein said adjusting the beam further comprises placing different thicknesses of material of a range modulator in the nozzle in the path of the beam to change the energies of at least a portion of the particles and achieve the Spread Out Bragg Peak.

4. The radiation therapy method of claim 1, wherein said adjusting the beam comprises placing different thicknesses of material of a range modulator in the nozzle in the path of the beam to change the energies of at least a portion of the particles and achieve the Spread Out Bragg Peak.

5. The radiation therapy method of claim 4, wherein the range modulator comprises a plurality of arms extending from a hub, the arms having non-uniform thicknesses, the method further comprising rotating the range modulator about the hub allowing the beam to pass through at least one of the arms.

6. The radiation therapy method of claim 5, further comprising:

moving the range modulator in a first direction between a position that is completely out of the path of the beam and a position that is in the path of the beam, wherein the first direction is transverse to the path of the beam; and moving the range modulator in a second direction different from the first direction and transverse to the path of the beam.

7. A radiation therapy method, comprising:

accelerating particles in a beam with an accelerator;

directing the beam of particles to a nozzle that is downstream of the accelerator; and in the nozzle, affecting energies of the particles in the beam to create a first adjusted beam that delivers a first dose with a Spread Out Bragg Peak (SOBP) along a first target line segment in a target volume, and to create a second adjusted beam that delivers a second dose with a second SOBP along a second target line segment in the target volume, wherein the second target line segment is displaced from the first target line segment.

8. The radiation therapy method of claim 7, wherein said affecting the energies of the particles in the beam comprises placing different thicknesses of material of a range modulator in the path of the beam in the nozzle to change the energies of at least a portion of the particles.

9. The radiation therapy method of claim 8, wherein the range modulator comprises a plurality of arms extending from a hub, the arms having non-uniform thicknesses, the method further comprising rotating the range modulator about the hub allowing the beam to pass through at least one of the arms.

10. The radiation therapy method of claim 8, further comprising moving the range modulator in a first direction between a position that is completely out of the path of the beam and a position that is in the path of the beam.

11. The radiation therapy method of claim 10, wherein the first direction is transverse to the path of the beam, the method further comprising moving the range modulator in a second direction different from the first direction and transverse to the path of the beam.

12. The radiation therapy method of claim 7, wherein said affecting the energies of the particles in the beam comprises placing different thicknesses of material of a range shifter in the path of the beam in the nozzle to affect the distance that the particles penetrate into the target volume.

13. The radiation therapy method of claim 12, wherein said affecting the energies of the particles in the beam further comprises placing different thicknesses of material of a range modulator in the path of the beam in the nozzle to change the energies of at least a portion of the particles.

14. A radiation therapy system, comprising:

a nozzle operable for delivering a beam of particles in a direction toward a target volume; and a control system coupled to the nozzle and comprising a computer system having a processor and memory, and operable for controlling the nozzle to aim the beam;

wherein the nozzle delivers a dose along a target line segment in the target volume to coincide with a position of the target volume, wherein the dose is delivered in a period of time short enough to counter uncertainties in the position due to the motion of the target volume.

15. The radiation therapy system of claim 14, wherein the dose is at least four grays and is delivered along the target line segment in less than one second.

16. The radiation therapy system of claim 14, wherein the nozzle comprises a beam energy adjuster in the path of the beam of particles in the nozzle to affect energies of the particles in the beam.

17. The radiation therapy system of claim 16, wherein the beam energy adjuster comprises a range modulator in the nozzle configured to place different thicknesses of material in the path of the beam to change the energies of at least a portion of the particles in the beam, wherein the range modulator is configured to move in a first direction between a position that is completely out of the path of the beam and a position in the nozzle that is in the path of the beam.

18. The radiation therapy system of claim 16, wherein the beam energy adjuster comprises a range shifter in the nozzle configured to place a different thickness of the material in the path of the beam to vary the distance that the particles penetrate into the target volume according to the motion of the target volume.

19. The radiation therapy system of claim 18, wherein the beam energy adjuster further comprises a range modulator in the nozzle configured to place different thicknesses of material in the path of the beam to change the energies of at least a portion of the particles in the beam, wherein the range modulator is configured to move in a first direction between a position that is completely out of the path of the beam and a position in the nozzle that is in the path of the beam.

* * * * *